United States Patent [19]

Miller

[11] 4,417,088

[45] Nov. 22, 1983

[54] OLIGOMERIZATION OF LIQUID OLEFINS

[75] Inventor: Stephen J. Miller, San Francisco, Calif.

[73] Assignee: Chevron Research Company, San Francisco, Calif.

[21] Appl. No.: 305,678

[22] Filed: Sep. 25, 1981

[51] Int. Cl.$^3$ .............................................. C07C 2/02
[52] U.S. Cl. .................................... 585/533; 585/530
[58] Field of Search ................ 585/517, 530, 533, 510

[56] References Cited

U.S. PATENT DOCUMENTS

| | | | |
|---|---|---|---|
| 3,325,465 | 6/1967 | Jones et al. ......................... | 260/94.9 |
| 3,756,942 | 9/1973 | Cattanach ........................... | 208/137 |
| 3,827,968 | 8/1974 | Givens et al. ....................... | 208/49 |
| 3,960,978 | 6/1976 | Givens ................................ | 585/531 |
| 4,211,640 | 7/1980 | Garwood et al. .................... | 208/255 |
| 4,227,992 | 10/1980 | Garwood et al. .................... | 208/46 |
| 4,238,318 | 12/1980 | Kouwenhoven et al. ........... | 208/137 |
| 4,289,607 | 9/1981 | Kokotailo ............................ | 585/533 |
| 4,324,940 | 4/1982 | Dessau ................................ | 585/533 |

*Primary Examiner*—Curtis R. Davis
*Attorney, Agent, or Firm*—D. A. Newell; S. R. La Paglia; W. L. Stumpf

[57] ABSTRACT

A new process for oligomerizing liquid olefins using intermediate pore size molecular sieves is disclosed.

17 Claims, 2 Drawing Figures

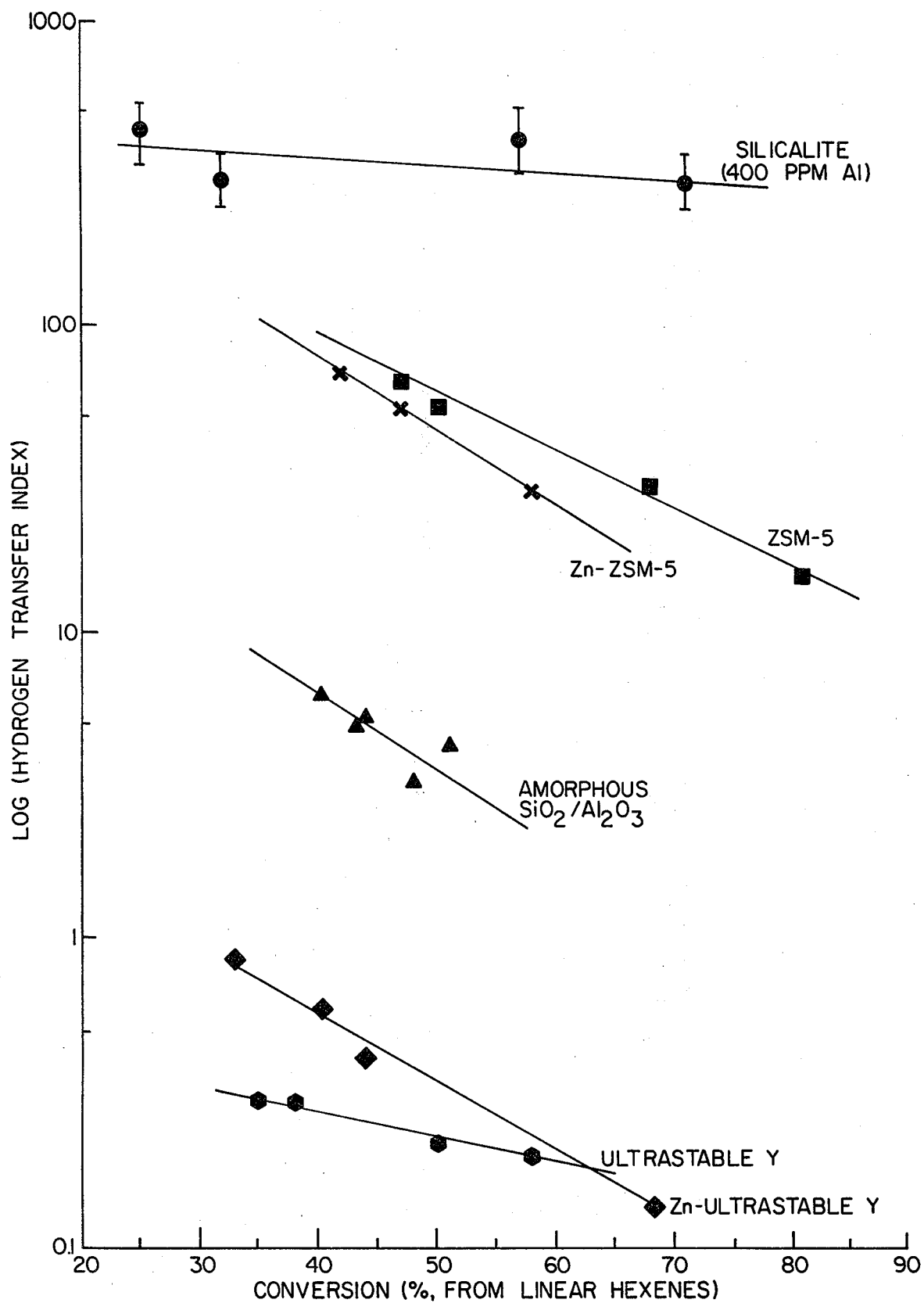
FIG._1.

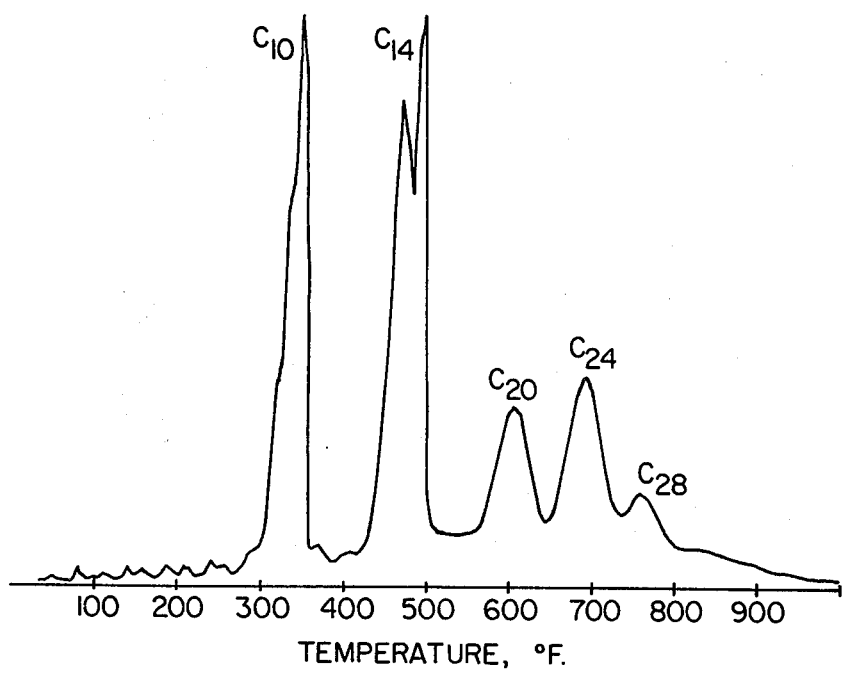
FIG._2.

OLIGOMERIZATION OF LIQUID OLEFINS

TECHNICAL FIELD

Heavy olefins are chemicals which are highly useful and desirable compounds, especially when they have only minor amounts of branching. These compounds can be used without further reaction as components of functional fluids such as lubricants, as viscosity index improvers in lubricants, as hydraulic fluids, as transmission fluids, and as insulating oils, e.g., in transformers to replace PCB containing oils. Heavy olefins can also undergo chemical reactions to produce surfactants which in turn can be used as additives to improve the operating characteristics of the compositions to which they are added (e.g., lubricating oils), or can be used as primary surfactants in highly important activities such as enhanced oil recovery. Among the most used surfactants prepared from heavy olefins are alkyl sulfonates and alkyl aryl sulfonates.

It can be appreciated that there is a continuing search for more efficient methods for preparing these highly desirable olefins.

The typical methods of preparing heavy olefins use 1-alkenes (alpha-olefins) as the reactants. In a typical process, 1-octene, 1-decene, 1-tetradecene or mixtures thereof are oligomerized and heavy olefin mixtures comprising trimers, tetramers and pentamers of the reactants are recovered. The processes are typically catalytic and typically use multiphase systems.

Standard oligomerization processes use phosphoric acid containing catalysts to prepare gasoline range materials. Three major modifications involving phosphoric acid catalysts include (1) quartz wetted with liquid phosphoric acid, (2) phosphoric acid impregnated pellets (e.g., kieselguhr) used in reaction chambers, and (3) phosphoric acid impregnated catalyst pellets packed in tubes surrounded by cooling water. Additionally, copper pyrophosphate has been used as a catalyst.

More recent processes for producing heavy olefins for synthetic lubricants, as opposed to gasoline range fuels, use boron trifluoride as the catalyst, together with promoters (e.g., $BF_3$-decanol or $BF_3$-acetic acid complexes), or with cocatalysts. Reaction conditions typically include temperatures of less than 100° C. and pressures of less than 7 bar. The reactions are carried out in solutions which contain the alkene reactants and the $BF_3$-complex or the cocatalyst. Gaseous $BF_3$ is typically added by bubbling through the solution. Cocatalysts include many organic compounds, such as esters, polyols, aliphatic alcohols, aliphatic ethers, aliphatic carboxylic acids, ketones, aldehydes and acid anhydrides.

A number of patents have issued relating to the preparation of aromatics from short chain olefins using highly active zeolites such as ZSM-5 (e.g., U.S. Pat. Nos. 3,756,942, Cattanach, Sept. 4, 1973; 3,827,968, Givens et al., Aug. 6, 1974; 3,960,978, Givens et al., June 1, 1976). Additionally, several patents disclose the preparation of gasoline and fuel oil range materials from short chain olefins such as propene and ethene (e.g., U.S. Pat. Nos. 4,227,992, Garwood et al., Oct. 14, 1980; 4,211,640, Garwood et al., July 8, 1980).

Even with the existence of phosphoric acid and zeolitic processes for making gasoline and of boron trifluoride processes for making heavy olefins, it can be appreciated that there is a continuing search for methods of heavy olefin preparation which use available materials, do not require solvent recovery steps or use of liquid solutions, and yet which are efficient.

I have discovered that under certain reactions conditions, medium to long chain alkenes can be polymerized over intermediate pore size crystalline molecular sieves to highly desirable heavier, longer chain alkenes. Surprisingly, intermediate pore size molecular sieves can catalyze these reactions even though they would have been expected to crack or aromatize the feed alkenes. My discovery is surprising because the art does not appear to have contemplated that longer chain materials could be produced using medium to long chain alkenes as reactants over these molecular sieves. The reactants have been thought to be too long to reach the catalytic active sites; and the active sites have been thought to be too active to do any more than shorten the long reactant chain.

Further, not only are heavier, longer chain alkenes produced, they have sufficient branching to have very low pour points, but not so much branching so as to have poor viscosity indexes. In addition, the product heavy olefins have excellent characteristics and reactivity for further processing to make surfactants useful in applications such as enhanced oil recovery and as lube oil additives. These advantages are surprisingly achieved using pressures high enough to keep the reactants in the liquid state while in the reaction zone and catalysts which have reduced hydrogen transfer activity.

TECHNICAL DISCLOSURE

My discoveries are embodied in a process for oligomerizing alkenes, comprising:

(a) contacting under oligomerization conditions a feed comprising one alkene which is a liquid under said oligomerization conditions with a catalyst comprising an intermediate pore size silicaceous crystalline molecular sieve substantially free of hydrogen transfer activity; and (b) recovering an effluent comprising oligomerized alkene.

My discoveries are further embodied in a process for oligomerizing alkenes, comprising:

(a) contacting under oligomerization conditions a feed comprising a mixture of alkenes wherein at least some of the alkenes in said alkene mixture are liquid under said oligomerization conditions with a catalyst comprising an intermediate pore size silicaceous crystalline molecular sieve substantially free of hydrogen transfer activity; and (b) recovering an effluent comprising alkene oligomers of said liquid alkenes.

My discoveries are still further embodied in a process for oligomerizing alkenes, comprising:

(a) contacting under oligomerization conditions a feed consisting of an alkene mixture wherein at least some of the alkenes in said feed are liquid under said oligomerization conditions with a catalyst comprising an intermediate pore size silicaceous crystalline molecular sieve substantially free of hydrogen transfer activity; and (b) recovering an effluent comprising alkene oligomers of said liquid alkenes.

The feeds used in my processes contain alkenes which are liquids under the conditions in the oligomerization reaction zone. Under standard operating procedures, it is normal both to know the chemical composition of feedstocks being introduced into a reaction zone and to set and control the temperature and pressure in the reaction zone. Once the chemical composition of a feedstock is known, the temperatures and hydrocarbon partial pressures which will maintain all or part of the feed as liquids can be determined using standard tables or routine calculations. Conversely, once the desired temperature and pressure to be used in the reaction zone are set, it becomes a matter of routine to determine what feeds and feed components would or would not be liquids in the reactor. These calculations involve using critical temperatures and pressures. Critical temperatures and pressures for pure organic compounds can be found in standard reference works such as CRC Handbook of Chemistry and Physics, International Critical Tables, Handbook of Tables for Applied Engineering Science, and Kudchaker, Alani, and Zwolinski, Chemical Reviews, 68, 659 (1968), all of which are incorporated herein by reference. The critical temperature for a pure compound is that temperature above which the compound cannot be liquified regardless of pressure. The critical pressure is the vapor pressure of the pure compound at its critical temperature. These points for several pure alkenes are listed below:

|  | $T_c$ °C. | (°F.) | $P_c$-atm | (bar) |
|---|---|---|---|---|
| ethene | 9.21 | (48.6) | 49.66 | (50.3) |
| propene | 91.8 | (197.2) | 45.6 | (46.2) |
| 1-butene | 146.4 | (295.5) | 39.7 | (40.2) |
| 1-pentene | 191.59 | (376.9) | 40 | (40.5) |
| iso-2-pentene | 203 | (397) | 36 | (36.5) |
| 1-hexene | 230.83 | (447.49) | 30.8 | (31.2) |
| 1-heptene | 264.08 | (507.34) | 27.8 | (28.2) |
| 1-octene | 293.4 | (560.1) | 25.6 | (25.9) |
| 1-decene | 342 | (648) | 22.4 | (22.7) |

It can be appreciated that at temperatures above about 205° C. (401° F.), pure $C_5$ and lower alkenes must be gaseous, while pure $C_6$ and higher alkenes can still be liquefied by applying pressure. Similarly, above about 275° C. (527° F.) pure $C_8$ and higher alkenes can be maintained in the liquid state, while pure $C_7$ and lower alkenes must be gaseous.

Typical feeds are mixtures of compounds. But even so, once the chemical composition of the feed is known, the critical temperature and pressure of the mixture can be determined from the ratios of the chemicals and the critical points of the pure compounds. See for example, the methods of Kay and Edmister in "Perry's Chemical Engineers Handbook, 4th Edition, pages 3-214, 3-215 (McGraw Hill, 1963), which is incorporated by reference.

Of course, the only constraint on the alkenes present in the feed and which are to react in the oligomerization reaction zone is that these alkenes be liquids under the conditions in the reaction zone (the conditions include a temperature of less than about 350° C.). The chemical composition of the alkenes can be varied to obtain any desired reaction mixture or product mix, so long as at least some of the alkene components of the feed are liquid.

The alkene chains can be branched. And, even though intermediate pore size molecular sieves are used, alkenes having quaternary carbons (two branches on the same carbon atom) can be used. But where quaternary carbons are present, it is highly preferred that the branches are methyl. It appears that even though the intermediate pore size molecular sieves do not admit quaternary carbon atoms into their pore structures, they have the capability of causing one of the quaternary substituents to migrate to a different position on the alkene chain, thereby forming two tertiary sites and an entity which can enter the intermediate sized pores.

The preferred alkenes are straight chain, or n-alkenes, and the preferred n-alkenes are 1-alkenes. The alkenes preferably have 8 or more carbon atoms, and more preferably have from about 9 to about 20 carbon atoms. Olefinic feeds which contain $C_{15}$–$C_{20}$ olefins are particularly suitable for use, especially since these alkenes have a chain length which is awkward for many uses (too short for lubes, too long for detergents).

One of the surprising discoveries which my invention embodies is that under certain reaction conditions, longer chain alkenes can be polymerized over intermediate pore size molecular sieves instead of being cracked to short chain compounds. Additionally, the oligomers produced from long n-1-alkenes are very highly desirable for use as lubricants. The oligomers have surprisingly little branching so they have very high viscosity indices, yet they have enough branching to have very low pour points.

The feed alkenes can be prepared from any source by standard methods. Often, suitable feeds are prepared from lower alkenes which themselves are polymerized into the appropriate range. Sources of such lower olefins can include FCC offgas, syngas (by use of CO reduction catalysts), low pressure, nonhydrogenative zeolite dewaxing, alkanols (using high silica zeolites), and dewaxing with crystalline silica polymorphs. Highly suitable n-1-alkene feeds, especially for preparing lubricating oil basestocks, can be obtained by thermal cracking of hydrocarbonaceous compositions which contain normal paraffins or by Ziegler polymerization of ethene.

By "intermediate pore size silicaceous crystalline molecular sieve," as used herein, is meant two classes of silica containing crystalline materials. The first class includes materials which, in addition to silica, contain significant amounts of alumina. These crystalline materials are usually called "zeolites," i.e., crystalline aluminosilicates. The second class of materials are essentially alumina free silicates. These crystalline materials can include crystalline silica polymorphs, e.g., silicalite, chromia silicates, e.g., CZM, and ferrosilicates, e.g., U.S. Pat. No. 4,238,318.

All of these materials have the ability of sorting molecules based on the size or the shape, or both of the molecules. The larger pore size materials will admit larger molecules than the smaller pore size materials. Intermediate pore size silicaceous crystalline molecular sieves have the unique characteristics of being able to differentiate between large molecules and molecules containing quaternary carbon atoms on the one hand, and smaller molecules on the other. Thus, the intermediate pore size materials have surprising catalytic selectivities by reason of their effective pore apertures, as well as highly desirable and surprising catalystic activity and stability when compared to larger pore size crystalline molecular sieves.

By "intermediate pore size," as used herein, is meant an effective pore aperture in the range of about 5 to 6.5 Angstroms when the molecular sieve is in the H-form. Molecular sieves having pore apparatus in this range tend to have unique molecular sieving characteristics. Unlike small pore zeolites such as erionite and chabazite, they will allow hydrocarbons having some branching into the molecular sieve void spaces. Unlike larger pore zeolites such as the faujasites and mordenites, they can differentiate between n-alkanes and slightly branched alkanes on the one hand and larger branched alkanes having, for example, quaternary carbon atoms.

The effective pore size of the molecular sieves can be measured using standard adsorption techniques and hydrocarbonaceous compounds of known minimum kinetic diameters. See Breck, *Zeolite Molecular Sieves*, 1974, (especially Chapter 8) and Anderson et al, J. Catalysis 58, 114 (1979), both of which are incorporated by reference.

Intermediate pore size molecular sieves in the H-form will typically admit molecules having kinetic diameters of 5.0 to 6.5 Angstroms with little hindrance. Examples of such compounds (and their kinetic diameters in Angstroms) are: n-hexane (4.3), 3-methylpentane (5.5), benzene (5.85), and toluene (5.8). Compounds having kinetic diameters of about 6 to 6.5 Angstroms can be admitted into the pores, depending on the particular sieve, but do not penetrate as quickly and in some cases are effectively excluded. Compounds having kinetic diameters in the range of 6 to 6.5 Angstroms include: cyclohexane (6.0), 2,3-dimethylbutane (6.1), m-xylene (6.1), and 1,2,3,4-tetramethylbenzene (6.4). Generally, compounds having kinetic diameters of greater than about 6.5 Angstroms do not penetrate the pore apertures and thus are not absorbed into the interior of the molecular sieve lattice. Examples of such larger compounds include: o-xylene (6.8), hexamethylbenzene (7.1), 1,3,5-trimethylbenzene (7.5), and tributylamine (8.1).

The preferred effective pore size range is from about 5.3 to about 6.2 Angstroms. Among the materials falling within this range are the zeolite ZSM-5, the crystalline silica polymorphs, silicalite and Ser. No. RE 29, 948 organosilicates, and the chromia silicate, CZM.

In performing adsorption measurements to determine pore size, standard techniques are used. It is convenient to consider a particular molecule as excluded if it does not reach at least 95% of its equilibrium adsorption value on the zeolite in less than about 10 minutes (p/po=0.5; 25° C.).

Examples of intermediate pore size siliceous crystalline molecular sieves include zeolites such as CZH-5 and members of the ZSM series, e.g., ZSM-5, ZSM-11, ZSM-12, ZSM-21, ZSM-23, ZSM-35, and ZSM-38. ZSM-5 is described in U.S. Pat. Nos. 3,702,886 and 3,770,614; ZSM-11 is described in U.S. Pat. No. 3,709,979; ZSM-12 is described in U.S. Pat. No. 3,832,449; ZSM-21 and ZSM-38 are described in U.S. Pat. No. 3,948,758; ZSM-23 is described in U.S. Pat. No. 4,076,842; ZSM-35 is described in U.S. Pat. No. 4,016,245; CZH-5 is disclosed in Ser. No. 166,863, Hickson, filed July 7, 1980. These patents and specifications are incorporated herein by reference. The intermediate pore size materials can include "crystalline admixtures" which are thought to be the result of faults occurring within the crystal or crystallite area during the synthesis of the zeolites. The "crystalline admixtures" are themselves zeolites but have characteristics in common, in a uniform or nonuniform manner, to what the literature reports as distinct zeolites. Examples of crystalline admixtures of ZSM-5 and ZSM-11 are disclosed and claimed in U.S. Pat. No. 4,229,424, Kokotailo, Oct. 21, 1980 (incorporated by reference). The crystalline admixtures are themselves intermediate pore size zeolites and are not to be confused with physical admixtures of zeolites in which distinct crystals or crystallites of different zeolites are physically present in the same catalyst composite or hydrothermal reaction mixture.

Other examples of intermediate pore size siliceous crystalline molecular sieves include crystalline silica polymorphs which, as described before, are essentially alumina free.

"Essentially alumina free," as used herein, is meant the product silica polymorph (or essentially alumina-free siliceous crystalline molecular sieve) has a silica:alumina mole ratio of greater than 200:1, preferably greater than 500:1, and more preferably greater than 1000:1. The term "essentially alumina free" 0 is used because it is difficult to prepare completely aluminum free reaction mixtures for synthesizing these materials. Especially when commercial silica sources are used, aluminum is almost always present to a greater or lesser degree. The hydrothermal reaction mixtures from which the essentially alumina free crystalline siliceous molecular sieves are prepared can also be referred to as being substantially aluminum free. By this usage is meant that no aluminum is intentionally added to the reaction mixture, e.g., as an alumina or aluminate reagent, and that to the extent aluminum is present, it occurs only as a contaminant in the reagents.

Intermediate pore size crystalline silicas include silicalite, disclosed in U.S. Pat. No. 4,061,724; the "Ser. No. RE 29,948 organosilicates" as disclosed in Ser. No. RE 29,948; and CZH-9, Ser. No. 264,767, Hickson, filed May 18, 1981. Intermediate pore size silicas, ferrosilicates and galliosilicates are disclosed in U.S. Pat. No. 4,238,318, Kouwenhoven et al, Dec. 9, 1980. Intermediate pore size chromia silicates, CZM, are disclosed in Ser. No. 160,618, Miller, filed June 28, 1980. All of these are incorporated by reference.

The most preferred molecular sieves are the zeolites ZSM-5, ZSM-11, and their crystalline admixtures, silicalite, Ser. No. RE 29,948 organosilicates, and CZM. Of course, these and other molecular sieves can be used in physical admixtures.

The siliceous crystalline molecular sieves must be substantially free of hydrogen transfer activity. High hydrogen transfer activity is typically present in a catalyst as a result of a high aluminum content (low silica:alumina mole ratio) in a molecular sieve component. If the silica:alumina ratio is low, the catalyst will tend to convert the olefinic products and reactants to paraffins and aromatics rather than to oligomerize them, thereby greatly reducing or eliminating the benefits of the present invention. (Hydrogen transfer activity is to be distinguished from hydrogenation activity, which would saturate the alkenes to produce the corresponding alkanes.) The hydrogen transfer activity of the molecular sieve can be substantially lessened by using essentially alumina free siliceous crystalline molecular sieves, and especially materials such as silicalite, the Ser. No. RE 29,948 organosilicates, and CZM.

Zeolitic siliceous crystalline molecular sieve catalysts can be made substantially more active and stable for oligomerization by including the Group IIB metals, zinc or cadmium. A primary characteristic of these substituents is that they are weak bases, and are not easily reduced. These metals can be incorporated into the catalysts using standard impregnation, ion exchange, etc., techniques. Other metals such as calcium and the rare earths may be included in the catalyst. If hydrogen is not added to the feed, Group VIII metals (such as nickel, cobalt, palladium, and platinum) as well as other metals (such as chromium, vanadium, titanium, manganese, and rhenium) may be included in the catalyst. Mixtures of these metals may also be present. Strongly basic metals such as the alkali metals are unsatisfactory as they poison substantially all of the polymerization sites on the zeolite. For this reason, the alkali metal content of the zeolite is less than 1%, preferably less than 0.1%, and most preferably less than 0.01%. The most preferred substituents for use are zinc and cadmium, of these zinc is preferred. The amount of zinc or cadmium used is typically from about 0.01 to 10 weight percent.

The use of zinc or zinc compounds as the substituent on the zeolitic molecular sieves, and even on the essentially alumina free materials, gives surprising stability, yields, and activity in the liquid olefin oligomerization processes described herein.

The substantial absence of hydrogen transfer activity can be determined using standard laboratory procedures.

The polymerization processes of the present invention are surprisingly more efficient with small crystallite sieve particles than with larger crystalline particles. Preferably, the molecular sieve crystals or crystallites are less than about 10 microns, more preferably less than about 1 micron, and most preferably less than about 0.1 micron in the largest dimension. Methods for making molecular sieve crystals in different physical size ranges are known to the art.

The molecular sieves can be composited with inorganic matrix materials, or they can be used with an organic binder. It is preferred to use an inorganic matrix since the molecular sieves, because of their large internal pore volumes, tend to be fragile, and to be subject to physical collapse and attrition during normal loading and unloading of the reaction zones as well as during the oligomerization processes. Where an inorganic matrix is used, it is highly preferred that the matrix be substantially free of hydrocarbon conversion activity. It can be appreciated that if an inorganic matrix having hydrogen transfer activity is used, a significant portion of the oligomers which are produced by the molecular sieve may be converted to paraffins and aromatics and to a large degree the benefits of my invention will be lost.

The reaction conditions under which the oligomerization reactions take place include hydrocarbon partial pressures sufficient to maintain the desired alkene reactants in the liquid state in the reaction zone. Of course, the larger the alkene molecules, the lower the pressure required to maintain the liquid state at a given temperature. As described above, the operating pressure is intimately related to the chemical composition of the feed, but can be readily determined. Thus, the required hydrocarbon partial pressures can range from 26 bar at 290° C. for a pure n-1-octene feed to about atmospheric pressure for a n-1-$C_{15}$-$C_{20}$ alkene mixture. It is important to remember that while one process may introduce a liquid feed into a reaction zone and obtain a liquid product, the conditions in the reaction zone may be such that the reactants and products are gaseous while in the reaction zone. In my process, both reactant and product are liquids under the conditions in the reaction zone, thus leading to a high residnce time of each molecule in the catalyst and thus to the very surprising oligomerization of molecules which the art has considered too large to function as reactants over intermediate pore size materials.

The reaction zone is typically operated below about 350° C. Above that temperature not only significant cracking of reactants and loss of oligomer product take place, but also significant hydrogen transfer reactions causing loss of olefinic oligomers to paraffins and aromatics take place. Liquid hourly space velocities can range from 0.05 to 20, preferably from 0.1 to about 4.

Once the effluent from the oligomerization reaction zone is recovered, a number of further processing steps can be performed.

If it is desired to use the long chain compounds which have been formed in lube oils as base stock, the alkene oligomers can be hydrogenated.

All or part of the effluent can be contacted with the molecular sieve catalyst in further reaction zones to further react unreacted alkenes and alkene oligomers with themselves and each other to form still longer chain materials. Of course, the longer the carbon chain, the more susceptible the compound is to being cracked. Therefore, where successive oligomerization zones are used, the conditions in each zone must not be so severe as to crack the oligomers. Preferably, the reaction conditions in each of the succeeding zones are less severe than in the oligomerization zone which immediately precedes it. Operating with oligomerization zones in series with decreasing severity can also make process control of the exothermic oligomerization reactions much easier.

One particularly desirable method of operation is to separate unreacted alkenes present in the effluent from the alkene oligomers present in the effluent and then to recycle the unreacted alkenes back into the feed.

The run life of the catalyst in the oligomerization reaction zone can be greatly and surprisingly increased by periodically stopping the flow of feed into the reaction zone and stripping the catalyst with a stripping gas (such as hydrogen, nitrogen, or water vapor).

FIGURES

FIG. 1 illustrates data showing differences between the hydrogen transfer indices of several catalysts as well as the response of the hydrogen transfer indices to fouling.

FIG. 2 shows the boiling point distribution of the product from codimerizing 1-decene and 1-tetradecene.

EXAMPLE 1

A series of experiments was performed to examine the hydrogen tranfer activity of molecular sieves. A feed pulse of fixed volume (0.5 microliter) from a heated Valco valve was carried into a small, fixed catalyst bed located in a stainless steel reactor. The reaction was entirely gas phase and isothermal. The hydrocarbon feed pulse was carried to the catalyst bed by a known velocity nitrogen stream at a high linear rate. The nitrogen stream was passed through a 4A/5A molecular sieve purifier before contacting the feed. The catalyst bed contained −250 mesh catalyst fines which, depending on the catalyst, were diluted with the same size mesh alumina. The diluent alumina was added as needed to reduce the catalyst activity so all catalysts could be measured at roughtly identical feed conversions. The catalyst was finally diluted (4:1) with 80–100 mesh, acid washed Alundum to improve catalyst dispersion and to help maintain a true isothermal bed temperature. Reactor pressure was controlled by an Annin valve.

The entire gas stream, containing the reacted feed pulse, was taken directly through heated lines to the injector splitter of a capillary gas chromatograph equipped with a flame ionization detector.

The reaction conditions include a catalyst temperature of 221° C. (430° F.), total pressure of 34.5 bar (500 psi) and a nitrogen carrier gas flow of 800 cc/min. at STP. The injection volume was 0.5 microliter. Hydrocarbon analysis was performed using a 50-meter OV-101 fused silica capillary column. The catalyst was continually exposed to the nitrogen carrier gas between injections.

The hydrogen transfer index calculated from the test results is the ratio of 3-methylpentenes to 3-methylpentane produced from a 1-hexene feed, with a linear hexene conversion from 30% to 70%.

The contact time was computed from the temperatures and pressure corrected linear velocity of the nitrogen carrier stream and the length and volume of the catalyst bed. The computed WHSV and catalyst/oil ratio were based solely on the active component content within the bed.

The catalysts tested are listed in Table 1.

TABLE 1

| | Catalyst | $SiO_2/Al_2O_3$ Mole Ratio |
|---|---|---|
| (A) | ZSM-5 | 78:1 |
| (B) | Silicalite | 230:1 |
| (C) | Silicalite | 2200:1 |
| (D) | Ultrastable Y | 6:1 |
| (E) | Dealuminated Mordenite | 63:1 |
| (F) | Amorphous $SiO_2/Al_2O_3$ | 54/46 (wt. ratio) |
| (G) | CZH-5 | 50:1 |

The results obtained are listed in Table 2. Experiments with Catalysts (A) and (B) were performed after impregnating the catalysts with 0.8 weight percent zinc.

The graph of FIG. 1 illustrates the differences in hydrogen transfer index for several catalysts, as well as the response of the hydrogen transfer index to the number of hexene injections, i.e., to the fouling of the catalyst. The higher the hydrogen transfer index, the lower the hydrogen transfer activity of the catalyst. The hydrogen transfer index should be above 10, preferably above 25.

EXAMPLE 2

An experiment was performed to produce lubricant oil range materials from shorter chain length hydrocarbons. A 50/50 (wt.) mixture of 1-decene (b.p. 338° F.) and 1-tetradecene (b.p. 419° F.) was contacted with a Zn-ZSM-5 catalyst (1% Zn) at 232° C. (450° F.), hydrocarbon pressure of 27.6 bar (400 psig) and LHSV of 1. The product had the boiling characteristics shown by the distillation graph of FIG. 2. When the 329° C.+ (625° F.+) fraction of the product was hydrofinished, the pour point was less than −6.7° C. (20° F.) and the viscosity index was 105.

EXAMPLE 3

The alkene, 1-decene, was oligomerized over Zn-ZSM-5 (1% Zn) at 204° C. (400° F.), hydrocarbon pressure of 27.6 bar (400 psig) and LHSV of 1. The 1-decene was 46% converted with about 2% selectivity to $C_9-$, about 75% to 80% selectivity to $C_{20}$ dimer, and about 11% selectivity to the $C_{21}+$ fraction which primarily comprised $C_{30}$ trimer.

EXAMPLE 4

An experiment was performed to examine dimerizing and trimerizing $C_{10}$ alkenes, $C_{15}$–$C_{20}$ alkenes, and their mixtures. The composition of the $C_{10}$ alkenes feedstock used was:

| | |
|---|---|
| 1-alkenes | 88% |
| branched 1-alkenes | 1% |
| branched internal olefins | 4% |
| unbranched internal olefins | 2% |
| diolefins | 4% |
| paraffins/naphthenes | 0.7%/0.3% |

The $C_{15}$–$C_{20}$ alkene fraction had substantially the same composition but with some $C_{21}+$. The reactions were performed over a Zn (1 wt.%) ZSM-5/alumina (65/35 wt.%) catalyst at 27.6 bar (400 psig).

TABLE 2

| Catalyst | 20% A 80% $Al_2O_3$ | 20% A 80% $Al_2O_3$ | 65% B | 65% C | 12% D 88% $Al_2O_3$ | 18% E 82% $Al_2O_3$ | 100% F | 100% G |
|---|---|---|---|---|---|---|---|---|
| Inj. Number | 3 | 3 | 3 | 2 | 3 | 1 | 2 | 1 |
| Catalyst Wt (mg Sieve) | 4.4 | 4.1 | 19 | 24 | 2.8 | 4.2 | 35 | 19.3 |
| Zn (0.8%): Yes/No | No | Yes | Yes | No | No | No | No | No |
| Alundum Dilution | 4:1 | 4:1 | 4:1 | 3:1 | 4:1 | 4:1 | 4:1 | 4:1 |
| Contact Time (sec) | 0.25 | 0.36 | 0.33 | 0.41 | 0.28 | 0.23 | 0.34 | 0.4 |
| WHSV (l/hr) | 1100 | 806 | 200 | 120 | 1500 | 1220 | 100 | 157 |
| Cat/Oil | 13 | 12 | 57 | 71 | 9 | 13 | 104 | 57 |
| Conversion From Linear Hexenes (%) | 47 | 42 | 41 | 56 | 38 | 48 | 43 | 53 |
| $K_{Hexenes}$ (l/sec) | 2.54 | 1.51 | 1.60 | 2.00 | 1.71 | 2.84 | 1.65 | 1.88 |
| Product Yield, Wt % | | | | | | | | |
| $C_4$ Minus | 13 | 12.6 | 14 | 13.3 | 3.5 | 17.1 | 0.3 | 12 |
| $C_5$ | 11 | 10 | 8.4 | 8.5 | 4.2 | 12.9 | 3 | 8 |
| $C_6$ | 57 | 58.8 | 62 | 53.6 | 63.2 | 55.7 | 76.4 | 73 |
| $C_7$ | 4 | 4.2 | 4.1 | 5.5 | 4.7 | 4.4 | 3.5 | 2 |
| $C_8$ | 7.5 | 5.6 | 5.4 | 7.9 | 5.9 | 5.2 | 4.1 | 3.7 |
| $C_9$ | 4 | 3.6 | 2.5 | 4.3 | 4.3 | 2.4 | 2.4 | 1.3 |
| $C_{10}+$ | 1.9 | 2.8 | 2.3 | 4.9 | 10.7 | 1.1 | 10.1 | 0.3 |
| Hydrogen Transfer Index | | | | | | | | |
| 3M-Pentenes/ 3M-Pentane | 66 | 70 | 105 | 500 | 0.30 | 1.0 | 5 | 6 |

| Hours On Stream | Temperature °C. (°F.) | LHSV | Conversion, % Feed to: | |
|---|---|---|---|---|
| | | | $C_{22}+$ | $C_9-$ |
| Initial Feed - 3:1 (v/v) $C_{15}-C_{20}:C_{10}$ | | | | |
| 25 | 232 (450) | 0.75 | 24 | 3 |
| 91 | 232 (450) | 0.50 | 32 | 1 |
| 139 | 232 (450) | 0.50 | 17 | <1 |
| At 140 hours, the feed was changed to 100% $C_{15}-C_{20}$ | | | | |
| 184 | 204 (400) | 0.50 | 26 | 2 |
| 231 | 182 (360) | 0.50 | 6 | <1 |

| | | | Conversion To: | | |
|---|---|---|---|---|---|
| | | | $C_{20}+$ | $C_{30}+$ | $C_9-$ |
| At 282 hours, the feed was changed to 100% $C_{10}$ | | | | | |
| 304 | 246 (475) | 0.50 | 27 | 9 | 4 |
| The catalyst was rejuvenated for 1 hour by stripping with hydrogen at 427° C. (800° F.). The unit was restarted with 100% $C_{10}$ feed. | | | | | |
| 24 | 218 (425) | 0.50 | 39 | 10 | 2 |
| 48 | 218 (425) | 0.50 | 42 | 11 | 2 |

These data show significant amounts of oligomerization with little cracking of products or reactants.

What is claimed is:

1. A process for oligomerizing alkenes, comprising:
   (a) contacting under oligomerization conditions a feed comprising one alkene which is a liquid under said oligomerization conditions with a catalyst comprsing an intermediate pore size silicaceous crystalline molecular sieve substantially free of hydrogen transfer activity selected from silicalite, an organosilicate disclosed in Ser. No. RE 29,948 and CZM; and
   (b) recovering an effluent comprising oligomerized alkene.

2. A process for oligomerizing alkenes, comprising:
   (a) contacting under oligomerization conditions a feed comprising a mixture of alkenes wherein at least some of the alkenes in said alkene mixture are liquid under said oligomerization conditions with a catalyst comprising an intermediate pore size silicaceous crystalline molecular sieve substantially free of hydrogen transfer activity selected from silicalite, an organosilicate disclosed in Ser. No. RE 29,948, and CZM; and
   (b) recovering an effluent comprising alkene oligomers of said liquid alkenes.

3. A process for oligomerizing alkenes, comprising:
   (a) contacting under oligomerization conditions a feed consisting of an alkene mixture wherein at least some of the alkenes in said feed are liquid under aid oligomerization conditions with a catalyst comprising an intermediate pore size silicaceous crystalline molecular sieve substantially free of hydrogen transfer activity selected from silicalite, an organosilicate disclosed in Ser. No. RE 29,948, and CZM; and
   (b) recovering an effluent comprising alkene oligomers of said liquid alkenes.

4. The process of claim 2 or 3 in which substantially all of the alkenes in said alkene mixture are liquids under said oligomerization conditions.

5. The process of claim 4 wherein said oligomerization conditions include a temperature lower than the critical temperature of the alkene having the lowest critical temperature of the alkenes in said alkene mixture, and include a pressure higher than the critical pressure of the alkene having the highest critical pressure of the alkenes in said alkene mixture.

6. The process of claim 1, 2, or 3 in which said oligomerization conditions include a temperature of less than about 350° C.

7. The process of claim 1, 2, or 3 wherein said alkenes comprise branched chain alkenes and wherein the branches of said branched chain alkenes are methyl branches.

8. The process of claim 1, 2, or 3 wherein said alkenes comprise n-alkenes.

9. The process of claim 8 wherein said n-alkenes are 1-alkenes.

10. The process of claim 8 wherein said alkenes contain eight or more carbon atoms.

11. The process of claim 10 wherein said alkenes contain from about 9 to about 20 carbon atoms.

12. The process of claim 1, 2, or 3 wherein said catalyst further comprises zinc or a compound thereof, nickel or a compound thereof, cadmium or a compound thereof, or mixtures thereof.

13. The process of claim 1, 2, or 3, further comprising the step of: hydrogenating said alkene oligomers.

14. The process of claim 1, 2, or 3, further comprising the steps of: periodically removing said catalyst from contact with said feed, stripping said catalyst with a stripping gas, and resuming said contacting under oligomerization conditions.

15. The process of claim 1, 2, or 3, further comprising the steps of: separating unreacted alkenes present in said effluent from alkene oligomers present in said effluent and recycling said unreacted alkenes into the feed for said contacting step.

16. The process of claim 1, 2, or 3, further comprising the step of: further contacting at least part of the unreacted alkenes and alkene oligomers present in said effluent with a catalyst comprising an intermediate pore size silicaceous crystalline molecular sieve substantially free of hydrogen transfer activity in at least one further reaction zone under further oligomerization conditions wherein said further oligomerization conditions are not so severe as to crack oligomers present in the effluent of said further reaction zone.

17. The process of claim 16 in which the further oligomerization conditions in said further reaction zone are less severe than the reaction conditions of the oligomerization reaction zone immediately preceding said further reaction zone.

* * * * *

UNITED STATES PATENT AND TRADEMARK OFFICE
CERTIFICATE OF CORRECTION

PATENT NO. : 4,417,088

DATED : November 22, 1983

INVENTOR(S) : Stephen J. Miller

It is certified that error appears in the above-identified patent and that said Letters Patent are hereby corrected as shown below:

Col. 4, line 59, "catalystic" should read --catalytic--.

Col. 4, line 65, "pore apparatus" should read --apertures--.

Col. 6, line 13, "alumina free" 0 is used" should read --alumina free is--.

Col. 7, line 64, "residnce" should read --high residence--.

Col. 8, line 50, "tranfer" should read --transfer--.

Col. 8, line 63, "roughtly" should read --roughly--.

Col. 11, line 31, "comprsing" should read --comprising--.

Col. 11, line 54, "under aid" should read --under said--.

Signed and Sealed this

Seventeenth Day of July 1984

[SEAL]

Attest:

GERALD J. MOSSINGHOFF

Attesting Officer   Commissioner of Patents and Trademarks